United States Patent [19]

Kühnert et al.

[11] Patent Number: 5,386,318

[45] Date of Patent: Jan. 31, 1995

[54] APPARATUS FOR HANDLING BIOLOGICAL SPECIMENS

[75] Inventors: Jürgen Kühnert; Peter Zimmermann; Armin Baumann; Wolfgang Krämer, all of Jena, Germany

[73] Assignee: Jenoptron Gesellschaft Für Optoelektronik Und Handling mbH, Jena, Germany

[21] Appl. No.: 60,815

[22] Filed: May 12, 1993

[30] Foreign Application Priority Data

Sep. 20, 1991 [DE] Germany ............................. 4131360

[51] Int. Cl.6 ....................... G02B 21/26; B65G 29/00; B65G 65/00
[52] U.S. Cl. .................................. 359/394; 359/391; 414/223; 414/744.8
[58] Field of Search ....................... 359/394, 391, 396; 414/223, 744.2, 744.8

[56] References Cited

U.S. PATENT DOCUMENTS

| | | | |
|---|---|---|---|
| 3,738,730 | 6/1973 | Binnings et al. | 359/391 |
| 3,851,972 | 12/1974 | Smith et al. | 359/391 |
| 4,055,259 | 10/1977 | Sibrava | 414/223 |
| 4,248,498 | 2/1981 | Georges . | |
| 4,453,807 | 6/1984 | Faulkner et al. . | |
| 4,582,191 | 4/1986 | Weigand | 359/394 |
| 4,807,984 | 2/1989 | Kurimura et al. . | |
| 4,832,555 | 5/1989 | Gordon | 414/223 |
| 4,871,290 | 10/1989 | Kaczynski et al. | 414/223 |
| 5,029,996 | 7/1991 | Carter | 359/369 |
| 5,187,976 | 2/1993 | Gossler et al. | 414/223 |
| 5,222,285 | 6/1993 | Horikawa | 414/223 |
| 5,226,778 | 7/1993 | Sekitani | 414/223 |

Primary Examiner—Jon W. Henry
Attorney, Agent, or Firm—Nils H. Ljungman & Associates

[57] ABSTRACT

Apparatus for handling biological specimens for a diagnostic device and an apparatus to load the diagnostic device, the diagnostic device including a transport system and a carousel bearing several cassettes containing biological specimens. By means of the mechanical separation of the carousel, transport system and diagnostic device, simultaneous, independent movement of the individual components is possible. Thus, tedious routine inspections for which a selection of biological specimens is necessary can be conducted very quickly and efficiently.

19 Claims, 7 Drawing Sheets

APPARATUS FOR HANDLING BIOLOGICAL SPECIMENS

This application is a Continuation-In-Part application of International Application No. PCT/DE92/00807, filed on Sep. 18, 1992, which claims priority from Federal Republic of Germany Patent Application No. P 41 31 360.7, filed on Sep. 20, 1991. International Application No. PCT/DE92/00807 was pending as of the filing date of U.S. application Ser. No. 08/060,815 and the U.S. was an elected state in International Application No. PCT/DE92/00807.

BACKGROUND OF THE INVENTION

1. Field of the Invention

The invention relates to a handling system for use with a diagnostic device for biological specimens. The handling system includes an apparatus to load the diagnostic device, including a transport system and a carousel bearing several cassettes containing specimens. The invention is of particular advantage if a selection of specimens according to defined criteria is required for tedious and time-consuming inspections.

2. Background Information

For some time, efforts have been made to automatically load diagnostic devices as efficiently as possible, in particular diagnostic devices intended for the automatic evaluation of specimens. An apparatus to automatically load such a unit is disclosed in U.S. Pat. No. 4,248,498. Here, only one supply cassette is loaded and unloaded, requiring frequent manual intervention in the process to change the supply containers. The diagnostic device in the solution disclosed therein is rigidly connected to the transport mechanism and the diagnostic area so that a simple adaptation of the handling system to another diagnostic device is essentially not possible. The long specimen advance distances and the relatively long time required to adjust the diagnostic device tend to result in considerable idle time in the process, during which no evaluation can take place. In German Patent No. 3 705 166, a process and apparatus for the automatic loading of a diagnostic device is disclosed, in which the use of a rotary table bearing cassettes tends to significantly reduce the frequency of cassette changes. Specimen handling is by means of the vacuum technique often used for the handling of wafers during the manufacture of circuits. The complexity of the apparatus is increased by the need for vacuum generation. At the same time, there tends to be a risk of vibration of the specimens and of dust settling on the specimens due to the turbulence of the air.

In the solution just described, the diagnostic device, diagnostic area and transport mechanism also form a solid unit. Thus, sorting of the specimens parallel to image analysis and adaptation of the handling system to another diagnostic device are essentially not possible.

OBJECT OF THE INVENTION

The object of the invention is to produce a handling system for use with a diagnostic device for biological specimens and an apparatus to load the diagnostic device, including a transport system and a carousel, bearing several cassettes containing specimens, which works as quickly and efficiently as possible.

SUMMARY OF THE INVENTION

The present invention teaches us to achieve the above object by means of a handling system for a diagnostic device for biological specimens wherein:
  the transport system includes a cassette extraction mechanism for the vertical positioning of the specimens in the cassettes, and a rotary arm mechanically separated from the carousel and the diagnostic device so that simultaneous, independent movement is possible; and
  there are identifiers to identify the specimens and specimen spaces.

An additional advantageous effect is the handling system can be easily adapted to another appraisal unit.

Further advantageous embodiments of the handling system according to the present invention are described hereinbelow.

In summary, one aspect of the invention resides broadly in apparatus for handling biological specimens and for providing the biological specimens to a biological diagnostic device for examination of the biological specimens, which biological specimens are disposed on biological receptacles, the apparatus comprising: an arrangement for storing the biological receptacles; an arrangement for moving the biological receptacles from the storing arrangement to the biological diagnostic device; an arrangement for transferring the biological receptacle means from the storing arrangement to the moving arrangement; an arrangement for transferring the biological receptacles from the transporting arrangement to the diagnostic device; and the moving arrangement comprising an arrangement for rotatably moving the moving arrangement between the storing arrangement and the biological diagnostic device.

A further object of the invention is to produce a microscope handling system with a microscope unit, electronic control and evaluation system and an apparatus to load the microscope, including a transport system and a carousel, bearing several cassettes containing specimens, which works as quickly and efficiently as possible and makes possible image evaluation simultaneous with a specimen sorting process.

The present invention teaches us to achieve the above object by means of a microscope handling system wherein:
  the transport system includes a cassette extraction mechanism for the vertical positioning of the specimens in the cassettes, and a rotary arm mechanically separated from the carousel and the microscope unit so that simultaneous, independent movement is possible;
  there are identifiers to identify the specimens and specimen spaces; and
  there is feedback from the electronic evaluation system to the apparatus to load the microscope.

An additional advantageous effect is the handling system can be easily adapted to another microscope.

Further advantageous embodiments of the microscope handling system according to the present invention are described hereinbelow.

BRIEF DESCRIPTION OF THE DRAWINGS

One possible embodiment of the microscope handling system according to the invention is described hereinbelow with reference to the accompanying drawings, wherein.

DESCRIPTION OF THE PREFERRED EMBODIMENTS

Figure 1:
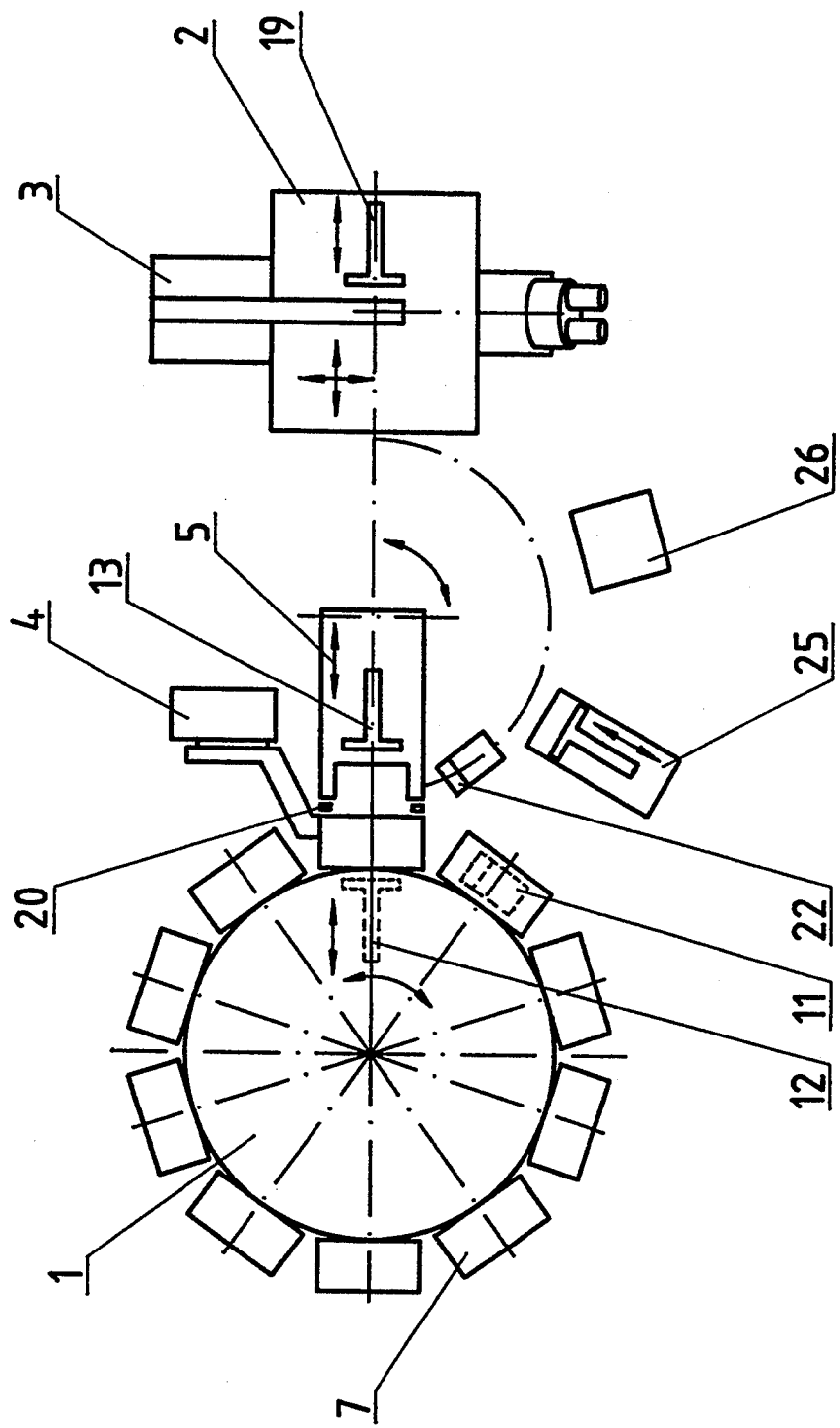
FIG. 1 shows the general arrangement of mechanical components.

The general arrangement of the mechanical components of an apparatus according to the invention, as shown in FIG. 1, is essentially comprised of the carousel 1 as a cassette platform, an x-y table 2 in the object zone of the microscope 3, and the transport system. The transport system preferably includes a cassette extraction mechanism 4 and a rotary arm 5 for the transport of specimens 6 between the carousel 1 and x-y table 2.

Figure 1A:
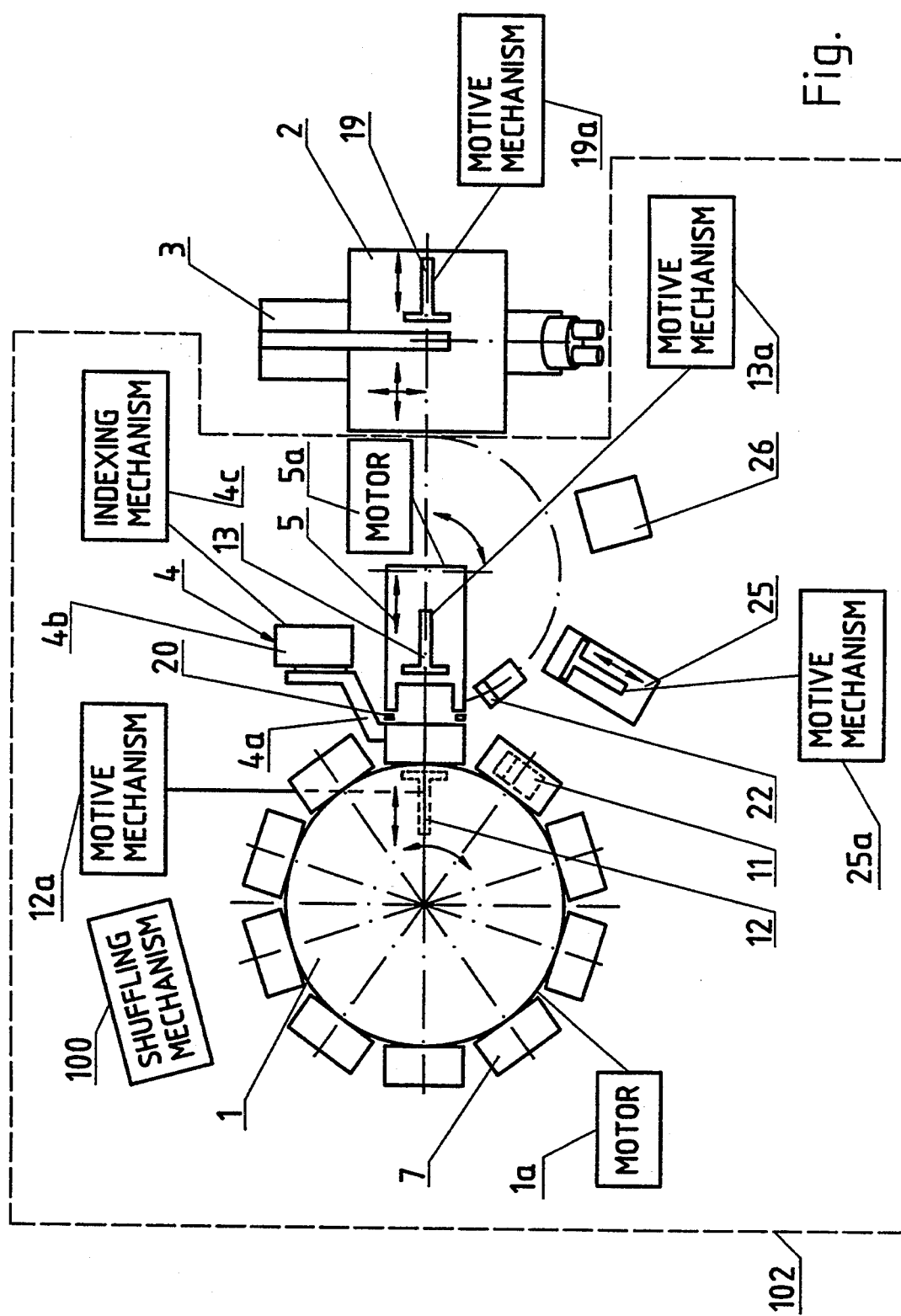
FIG. 1a is essentially the same as FIG. 1 but references additional components.
Figure 2:
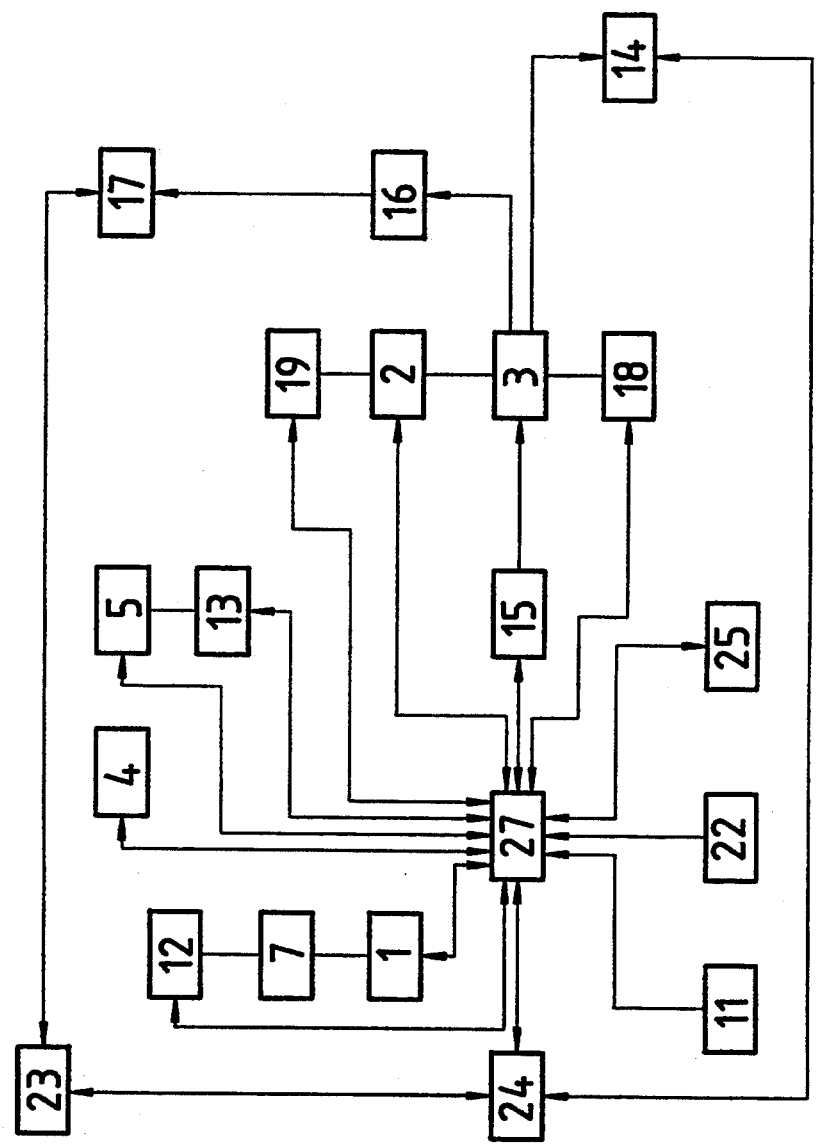
FIG. 2 is a block circuit diagram.

As shown in FIG. 1a, carousel 1, rotary arm 5, and cassette extraction mechanism 4 are all preferably mounted on a common frame or platform 102, wherein frame or platform 102 is preferably separate from microscope 3. It is also conceivable to place microscope 3 on frame or platform 102, or to even provide frame or platform 102 with an arrangement for interchangeably accommodating different microscopes 3. As shown, cassette extraction mechanism 4 preferably includes arm 4a, motor 4b and indexing mechanism 4c, each of which will be described more fully below. As will also be described more fully below, specimen slides, or pushers, 12, 13, 19 and 25 are preferably provided, as well as a shuffling mechanism 100. Each pusher 12, 13, 19 and 25 is preferably provided with a corresponding motive mechanism, indicated at 12a, 13a, 19a and 25a. Additionally, a suitable motor 1a is preferably provided to drive the rotation of carousel 1 and another suitable motor 5a is preferably provided to drive the rotation of rotary arm 5.

Figure 3:
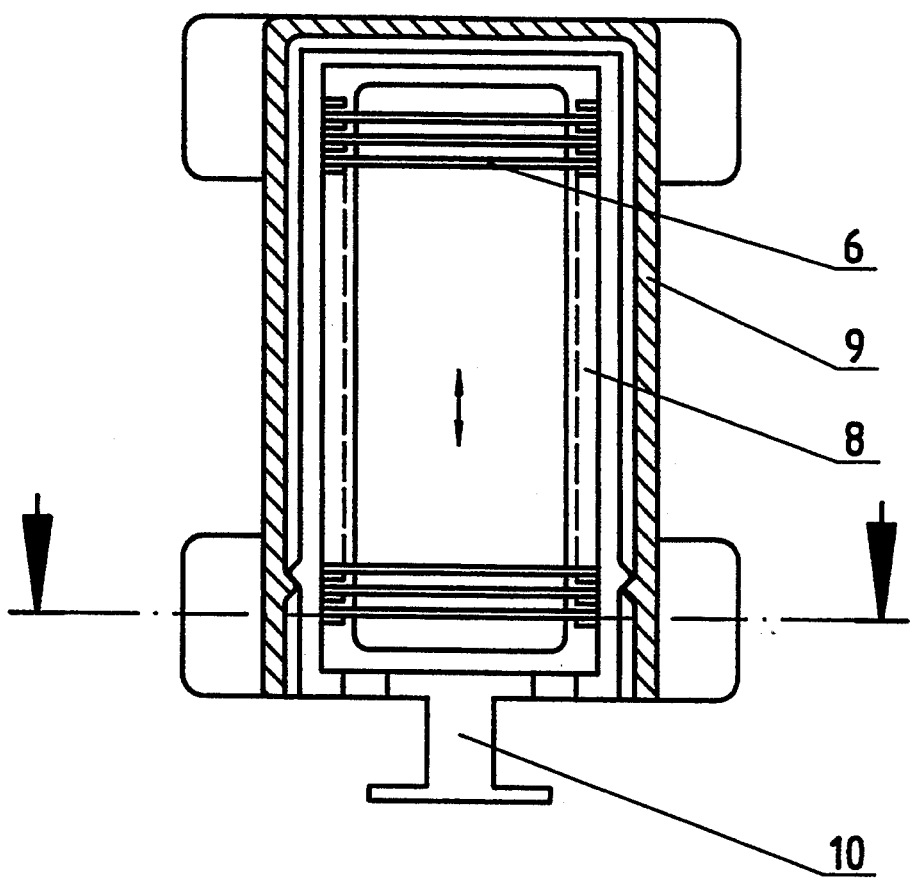
FIG. 3 is a side view of a cassette shown in cross-section.
Figure 4:
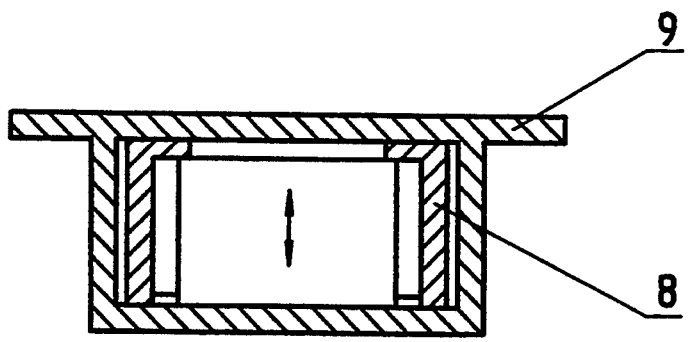
FIG. 4 is a plan view of a cassette in cross-section.
Figure 5:
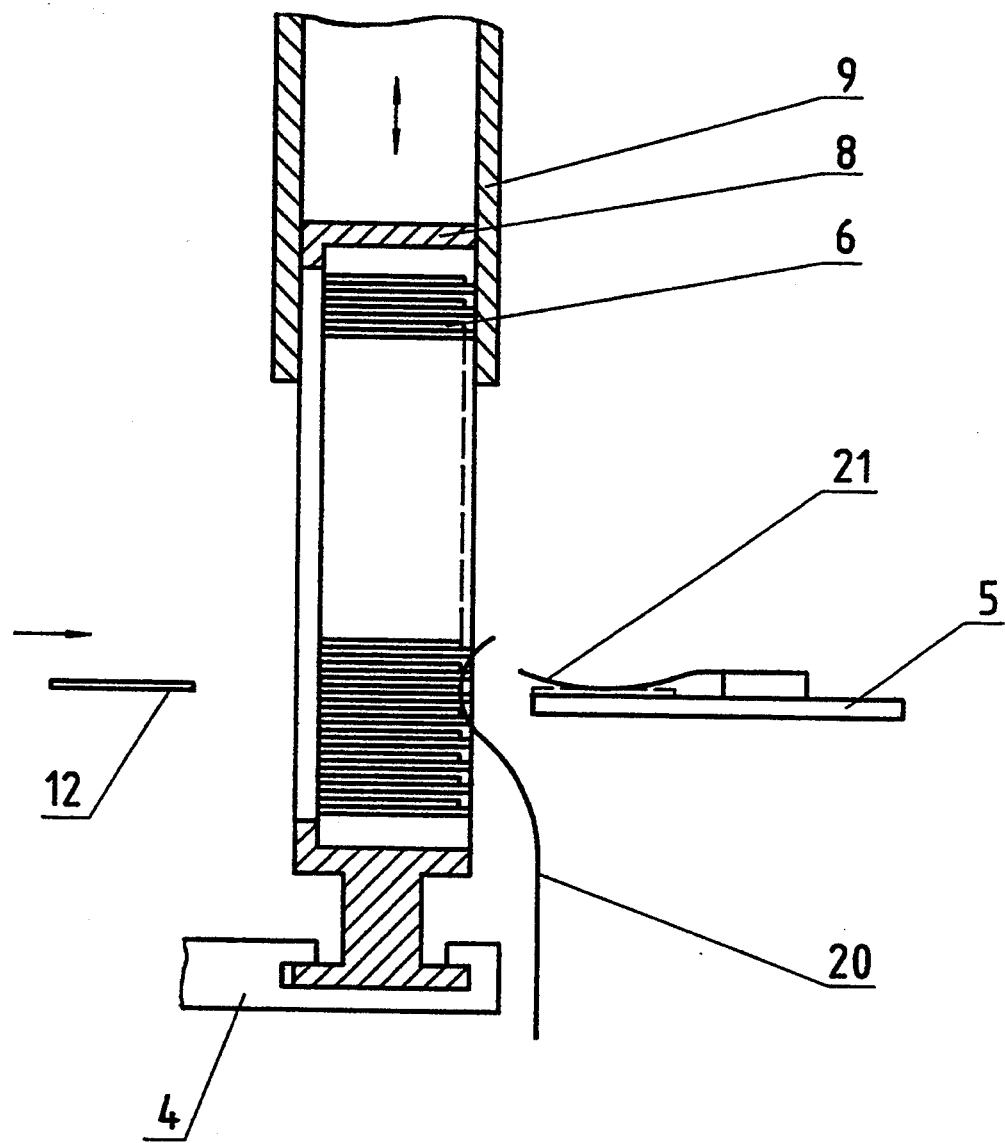
FIG. 5 shows a cassette in position for the loading and unloading of specimens.

The representation of a cassette loaded with specimens 6, in FIGS. 3 through 5, serves to better illustrate how the transport mechanism works.

Preferably, each cassette 7, such as a microscope slide holding arrangement, includes an inner portion 8, in which the specimens, or slides, or other components, 6 are preferably stacked horizontally, and a case 9 which is preferably fastened to the carousel 1 by means of a guide. At the same time, the case 9 essentially serves as mechanical protection and protection against dust. Preferably, by means of a handle 10, the inner portion 8 can be withdrawn from the case 9, which case is preferably open on one end. When the cassette 7 is closed, the case 9 and the inner portion 8 are locked together. The cassette 7 can thus also be used as a storage container.

Figure 3A:
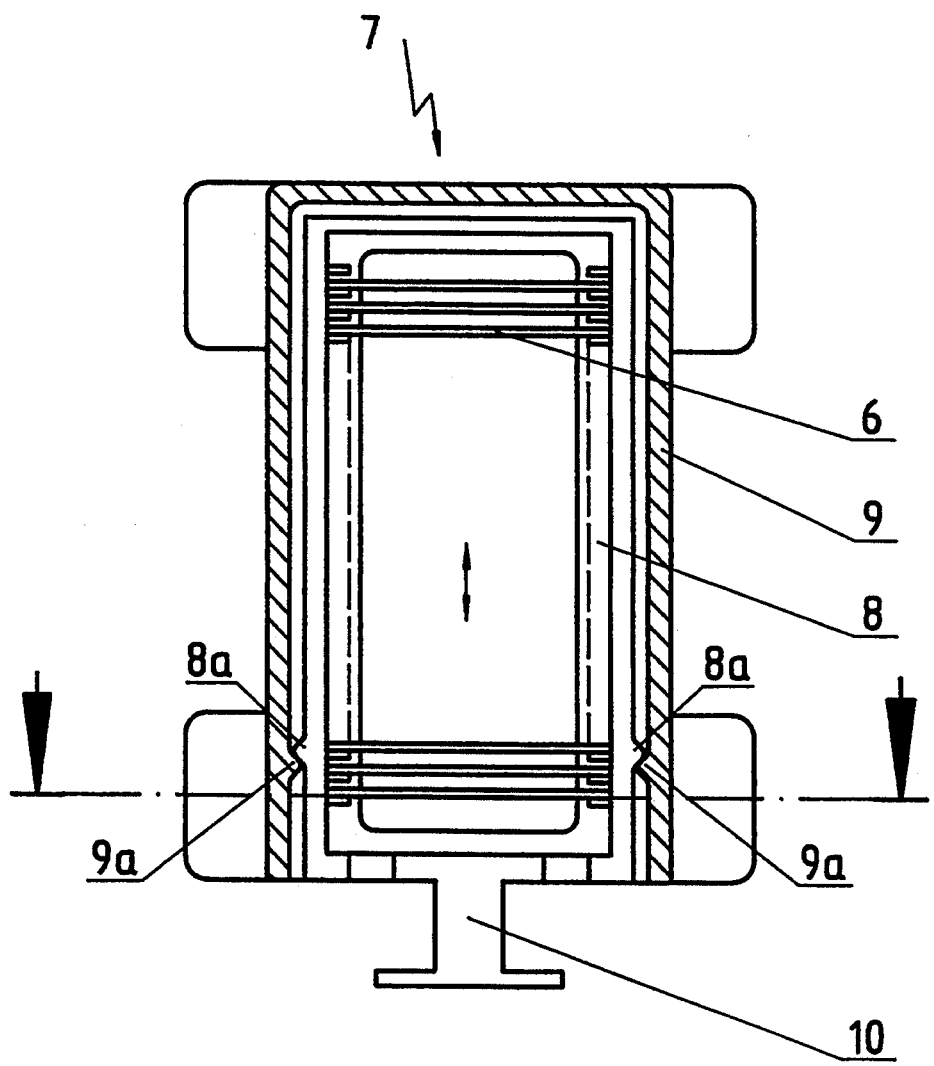
FIG. 3a is essentially the same view as FIG. 3 but references additional components.
Figure 4A:
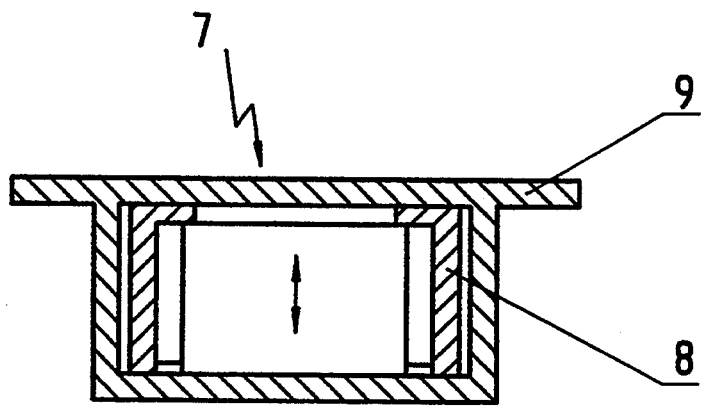
FIG. 4a is essentially the same view as FIG. 4 but references additional components.

Thus, in accordance with a preferred embodiment of the present invention, each cassette 7 preferably includes two interlocking components in the form of inner portion 8 and case 9, wherein inner portion 8 is preferably slidably disposed within case 9. Inner portion 8 is preferably configured to hold several horizontally stacked specimens 6. Preferably, case 9 is open on a lower end thereof in order to permit the withdrawal of inner portion 8 from within case 9. The interlocking of case 9 and inner portion 8 may essentially be achieved by any suitable means. One possibility for achieving such interlocking is shown in FIG. 3a, wherein inner portion 8 may include protrusions 8a and case 9 may include protrusions 9a. Preferably, protrusions 8a and 9a are configured such that, when inner portion 8 is inserted into case 9, an interlocking between inner portion 8 and case 9 is achieved yet allows the removal of inner portion 8 from case 9 when a downward force, such as a force from extraction mechanism 4, is applied to inner portion 8.

The carousel 1 essentially makes it possible to rotate the desired cassettes 7 over the cassette extraction mechanism 4. Preferably, during rotation of carousel 1, labels attached to the handles 10 of the cassettes 7 pass over a cassette identifier 11. If a cassette 7 is rotated into the cassette extraction mechanism 4, the inner portion 8 is preferably removed from the case 9 and the selected specimen 6 is positioned for the first specimen slide, or pusher, 12 and the rotary arm 5. The first specimen slide then preferably pushes the specimen out of the cassette 7 onto a free end of the rotary arm 5, where the specimen is secured preferably by two retaining springs 21. Preferably, the specimens 6 released from the case 9 are prevented from falling out by means of preferably two leaf springs 20 located below the first specimen slide 12. Essentially, the use of a rotary arm 5 for the transport of the specimens 6 makes it possible to cover large distances with short sliding movements. In turn, short sliding movements make possible the use of simple guidance and transport systems, without which there is a risk of jamming or binding of the guidance system for the slide and the specimen 6.

Figure 5A:
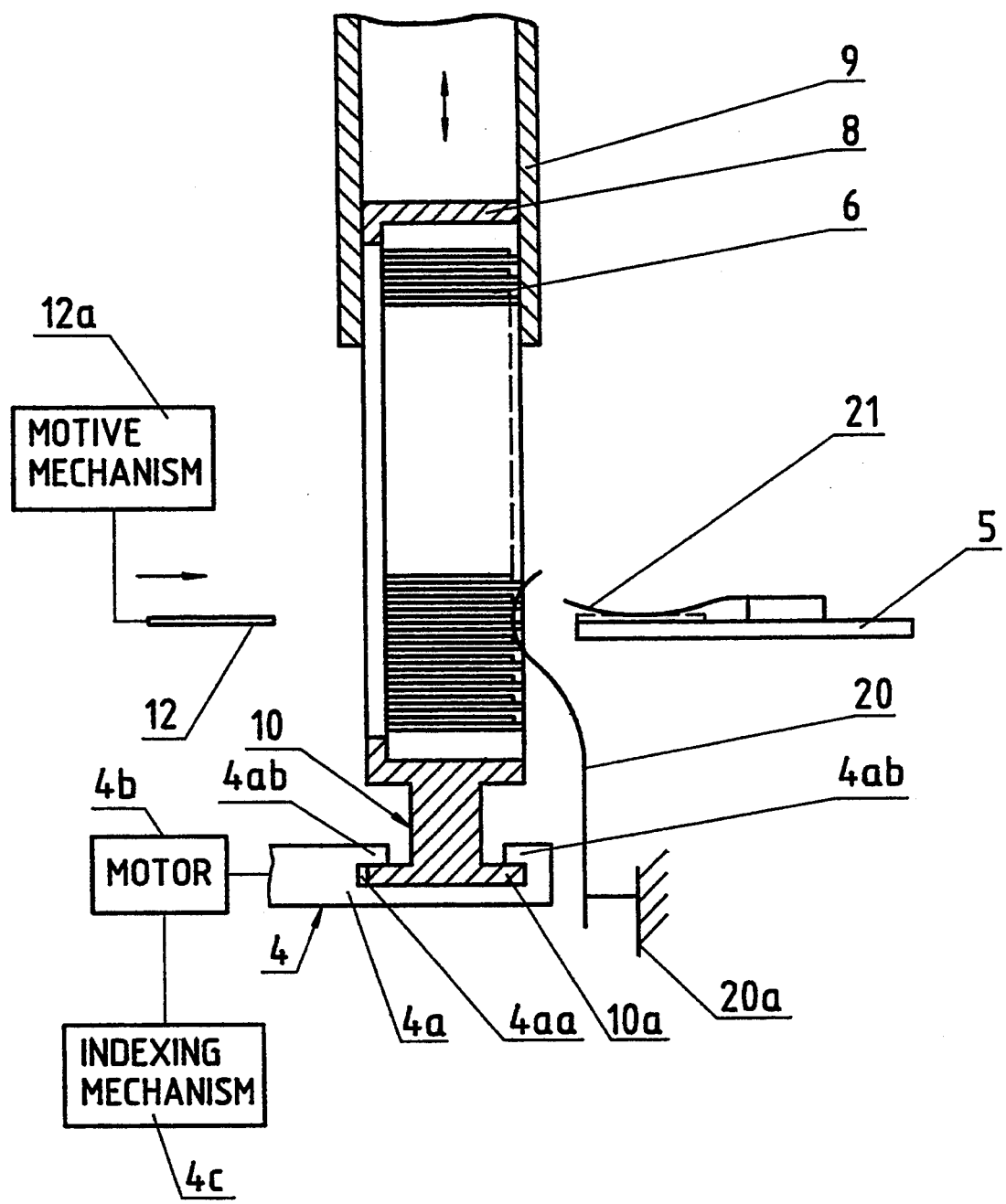
FIG. 5a is essentially the same view as FIG. 5 but references additional components.

As shown in FIG. 5a, leaf springs 20 may preferably be mounted, at one end thereof, on a block or other mounting surface 20a. Such a block or mounting surface 20a may be embodied by a protrusion from frame or platform 102, or may be embodied by a surface of frame of platform 102.

As shown, carousel 1 is preferably configured to hold several cassettes 7 about its periphery; in the embodiment illustrated in FIG. 1, carousel 1 is configured to hold ten cassettes 7, all of which are preferably equidistantly spaced from one another about the periphery of carousel 1. Essentially, any suitable arrangement may be used to mount cassettes 7 on carousel 1, such as a bolt arrangement or a bracket arrangement.

Preferably, at least one label (not shown) is provided on a portion of each cassette 7, such as on an underside portion of inner portion 8, and possibly on the underside of the handle 10 of inner portion 8. A label identifying device, or "cassette identifier", indicated at 11, may preferably be provided to detect the passage of a label therepast.

Cassette extraction mechanism 4 is preferably configured such that, when a desired cassette 7 arrives at extraction mechanism 4, the mechanism will pull inner portion 8 of cassette 7, via handle 10, downwardly and out from case 9. As shown in FIG. 5a, in a preferred embodiment of the present invention, arm 4a of cassette extraction mechanism 4 preferably includes a recessed area 4aa for accommodating a lower, flanged portion 10a of handle 10. Recessed area 4a is preferably shaped to essentially prevent vertical movement of the handle 10 with respect to recessed area 4aa but to allow horizontal movement, at least in the direction of rotation of carousel 1, of handle 10 with respect to recessed area 4aa. Thus, as shown, the handle 10 may preferably be shaped in such a manner that, when a cassette 7 is displaced towards cassette extraction mechanism 4, the lower, flanged portion 10a of handle 10 slides into the recess 4aa. Once in the recess 4aa, handle 10 is preferably confined in a vertical direction by means of protruding portions 4ab, which protruding portions 4ab preferably overlap portions of the lower, flanged portion 10a of handle 10.

The downward movement of arm 4a preferably takes place by means of a suitable motor 4b. Furthermore, an indexing mechanism 4c is preferably provided to ensure that the arm 4a is only moved downwardly to such an extent that the desired specimen 6 is appropriately aligned for being transferred to rotary arm 5. Of course, within the scope of the present invention, other suitable means may be provided for enacting a downward movement of specimens 6. One such possibility may be a linear transducer associated with cassette extraction mechanism 4. Conceivably, a rotary transducer may also be used in conjunction with the motor 4b.

Once inner portion 8 has been extracted by extraction mechanism 4, the desired specimen 6 for viewing is preferably positioned adjacent a first specimen slide 12 and rotary arm 5. Thence, preferably, the first specimen slide 12 will slidingly push that specimen 6 onto rotary arm 5. In a manner well known to those of ordinary skill in the art, the specimen 6 may preferably be secured by two retaining springs 21 on rotary arm 5.

Preferably, as shown in FIG. 1, rotary arm 5 is preferably configured to be a straight arm being mounted at a locus of rotation at one end of the arm. Thus, rotary arm 5 is preferably essentially mounted to move in the manner of the hand of a clock, in either a clockwise or a counterclockwise direction. It will be appreciated that the provision of a rotary arm 5 essentially precludes the need for inordinately large sliding movements in that, essentially, the transfer of a specimen 6 from inner portion 8 of cassette 7 to x-y table 2 entails a short sliding movement of specimen 6, followed by a rotation of arm 5 towards x-y table 2, followed by another short sliding movement of specimen 6.

Preferably, after the x-y table 2 of the microscope 3 is moved into the transfer position, the rotary arm 5 swings to the microscope 3 and the second specimen slide, or pusher, 13 on the rotary arm 5 preferably pushes the specimen 6 onto the x-y table 2. This slide apparatus is therefore preferably oriented perpendicular to the longitudinal direction of the specimen 6. In this manner, sliding distances and times can be minimized. Lying on the x-y table, the specimen is preferably moved into the beam path of the microscope 3.

In other words, to enable the transfer of a transported specimen 6 from rotary arm 5 to x-y table 2, x-y table 2 is preferably moved into a "transfer position", that is, a position wherein the transfer of specimen 6 from rotary arm 5 to table 2 is facilitated. This movement of x-y table 2 from an initial rest position to the "transfer" position preferably takes place before rotary arm 5 reaches the vicinity of microscope 3; however, it is conceivable to move x-y table 2 simultaneously with the arrival of rotary arm 5 at microscope 3 or even after the arrival of rotary arm 5 at microscope 3. The specimen 6 may be moved into the beam path of the microscope 3 by pusher 13 but may alternatively be moved into the beam path of the microscope 3 by a different displacement mechanism once on the x-y table 2.

In the embodiment described herein, it is essentially advantageous if the microscope 3 is an inverse microscope. In accordance with the optical arrangement, the specimens 6 can then essentially be seated without difficulty on rails on the side bearing the specimen 6. Of course, the microscope 3 may conceivably include a type of seat for the specimen other than rails.

Thus, essentially, in accordance with the present invention, a relationship between the microscope objective and the specimen 6 is created which is nearly independent of the thickness of the slide and the microscope 3 can be prefocused to the height of the mounting rails. The time required for automatic focusing and thus for the entire process is thereby reduced. An autofocus unit 14 is preferably placed on one of the optical outputs of the microscope 3. Such an autofocus unit 14 preferably provides the control signals for the focus motor 15. When the microscope 3 is focused, the image can be processed by means of the image input camera 16, which may preferably be a COD camera, and an image processing computer 17. Electric motors and two filter changers 18, wherein the filter changers preferably hold four filters each, can preferably be used to insert various combinations of filters. When image input is complete, the next site on the specimen 6 can preferably be brought into position and focused. The specimen can thus be scanned in a meandering pattern, for example.

After analysis of the specimen 6, the x-y table 2 is preferably returned to the transfer position and a third specimen slide 19 pushes the specimen 6 onto the rotary arm 5. Preferably, the rotary arm is rotated and the specimen 6 is pushed back into the cassette 7 by means of the second specimen slide 13. The next specimen 6 can then be moved into position and slid out. Preferably, with each rotation, the rotary arm 5 passes over a specimen identifier 22. Essentially, recognition of the specimens 6 and the cassettes 7 by means of the respective identifier makes possible not only a correspondence between the specimens and the analyzed images, but also the sorting of the specimens 6 in the carousel 1.

Thus, in accordance with a preferred embodiment of the present invention, a specimen identifier 22 is preferably provided which is able to identify a specimen 6 as the specimen 6 is displaced therepast. To achieve this, there may be provided at carousel 1 a sensing mechanism which can detect the absence of a specimen 6 from cassette 7 and, more particularly, detect the particular space from which such a specimen is absent. Accordingly, communication may be provided between such a sensing mechanism and specimen identifier 22 such that, when a specimen 6 passes identifier 22, it is possible to determine the precise specimen 6 which is being transported. Alternatively, each specimen 6 may be labelled in a manner which can be scanned or detected by the specimen identifier 22. As will be discussed herebelow, specimen identifier 22 is preferably configured to supply information regarding the recognition of the specimens 6 to a processing system, which processing system will thence preferably process information regarding the sorting of the specimens 6 in carousel 1 and the correspondence between specimens 6 and analyzed images.

In accordance with a preferred embodiment of the present invention, a host computer 23 makes it possible to input the control commands and output all commands received. The host computer 23 is preferably configured to organize the work of all of the computers in the system.

Preferably, a control computer 24 coordinates and monitors all electromechanical processes which take place via the electronic control system 27, motors and transmissions. Preferably, a system of photo-optics and limit switches indicate when the defined position has been reached as well as errors. Mechanical interference, such as jarring and vibrations, can be eliminated by means of the mechanical separation of the apparatus to load the microscope and the microscope layout. Furthermore, simultaneous, independent movement of the individual components is also possible which, for example, makes it possible to sort the specimens 6 within the cassettes 7 or also from one cassette 7 to another simultaneously with the image input process. For this purpose, not only are the specimens 6 and cassettes 7 preferably encoded, but also the specimen and cassette spaces, so that each specimen 6 can be assigned to a cassette 7 and each cassette 7 to a cassette space.

In order to sort the specimens 6 within the cassettes 7, or from one cassette to another, a shuffling mechanism 100 may be provided at the periphery of carousel 1, as shown in FIG. 1a. Such a shuffling mechanism 100 may preferably be configured to temporarily store one or more specimens 6 from a cassette 7 and then reinsert such a specimen or specimens 6 into either the same cassette 7 or another cassette 7. Conceivably, the same function may be accomplished by intermediate storage components 25 and 26, which components are described more fully below. In other words, possibly, the sorting of specimens 6 within an individual cassette 7 or from one cassette 7 to another may be accomplished by either or both of a shuffling mechanism 100 and the intermediate storage components 25 and 26, and such sorting may take place during image input from another specimen 6 at microscope unit 3.

Preferably, host computer 23 is used to manage the cassettes 7, specimens 6 and the specimen and cassette spaces. In accordance with specified parameters, sorting can take place automatically according to the results of the analysis of the images.

In other words, information entering host computer 23 from a variety of sources, such as from identifiers 11 and 22, and from specimen spaces in each cassette, can preferably be processed by the host computer 23 to aid in sorting.

By using the rotary arm 5 as the means of transport, several intermediate storage positions 25 or containers 26 can preferably be located tangentially to the pivoting range of the rotary arm 5, with only a small amount of design effort. In this manner, sorting can be conducted more efficiently. Particularly, unusable specimens 6 can easily be placed in a storage container. This container can also be fastened directly to the x-y table 2 opposite the third specimen slide 19, whereby an additional transfer to the rotary arm 5 would essentially not be necessary. Intermediate storage position may also preferably include an indexing mechanism, similar to indexing mechanism 4a.

In a preferred embodiment of the present invention, a cover with a safety contact over the carousel can be provided to prevent the removal of cassettes 7 during a sorting process. If the cover is opened, the carousel 1 again rotates past all of the cassette spaces and assigns the current cassette 7 data to the spaces on the basis of the information on the labels of the cassette 7.

One feature of the invention resides broadly in the microscope handling system with a microscope unit, electronic control and evaluation system and an apparatus to load the microscope, consisting of a transport system and a carousel 1, bearing several cassettes 7 containing specimens 6, characterized by the fact that the transport system consists of a cassette extraction mechanism 4 for the vertical positioning of the specimens 6 in the cassettes 7 and a rotary arm 5 mechanically separated from the carousel 1 and the microscope unit so that simultaneous, independent movement of the individual components is possible; there are identifiers to identify the specimens and specimen spaces and there is feedback from the electronic evaluation system to the apparatus to load the microscope.

Another feature of the invention resides broadly in the microscope handling system, characterized by the fact that the identifier to identify the specimens is located below the pivoting of the rotary arm.

Yet another feature of the invention resides broadly in the microscope handling system, characterized by the fact that there is a cassette identifier 11 for recognition of the cassettes.

Still another feature of the invention resides broadly in the microscope handling system, characterized by the fact that the cassette identifier 11 is located below the carousel 1.

Yet still another feature of the invention resides broadly in the microscope handling system, characterized by the fact that there is an identifier for recognition of the cassette spaces.

Another feature of the invention resides broadly in the microscope handling system, characterized by the fact that there are temporary storage areas 25 and/or containers 26 tangential to the pivoting range of the rotary arm.

Still another feature of the invention resides broadly in the microscope handling system, characterized by the fact that the cassette extraction mechanism 4 has at least one leaf spring 20 which secures the released specimens 6.

Yet still another feature of the invention resides broadly in the microscope handling system, characterized by the fact that the microscope of the microscope unit is an inverse microscope.

Still yet another feature of the invention resides broadly in the microscope handling system, characterized by the fact that the cassettes 7 are suitable for storage of the specimens 6.

U.S. Pat. No. 4,248,498, which issued to Georges on Feb. 3, 1991, contains examples of the following components, which may be utilized in accordance with the embodiments of the present invention: x-y table; motor for positioning an x-y table; specimen slide, or pusher, including motive mechanism therefor; automatic focusing unit.

Examples of inverse microscopes, which may be utilized in accordance with the embodiments of the present invention, may be found in the following U.S. Pat. No. 4,625,677, which issued to Neher on Dec. 2, 1986; and U.S. Pat. No. 4,619,503, which issued to Reinheimer et al. on Oct. 28, 1986.

Examples of image processing arrangements, which may be utilized in accordance with the embodiments of the present invention, may be found in the following U.S. Pat. No. 5,134,288, which issued to Van Dijck on Jul. 28, 1992; U.S. Pat. No. 4,866,273 which issued to Kobayashi et al. on Sep. 12, 1989; and U.S. Pat. No. 4,700,298, which issued to Palcic et al. on Oct. 13, 1987.

Examples of CCD cameras, which may be utilized in accordance with the embodiments of the present invention, may be found in the following U.S. Pat. No. 5,065,029 to Krivanek, which issued on Nov. 12, 1991; U.S. Pat. No. 4,945,220 to Mallory et al., which issued on Jul. 31, 1990; and U.S. Pat. No. 4,680,635 to Khurana, which issued on Jul. 14, 1987.

Examples of arrangements for sorting and/or shuffling specimens, which may be utilized in accordance with the embodiments of the present invention, may be found in the following U.S. Pat. No. 4,936,329, which issued to Michael et al. on Jun. 26, 1990; U.S. Pat. No. 4,732,467, which issued to Sweeney on Mar. 22, 1988; and U.S. Pat No. 4,695,727, which issued to Brierley, et al. on Sep. 22, 1987.

Examples of arrangements for encoding, which may be utilized in accordance with the embodiments of the present invention, may he found in the following U.S. Pat. No. 4,732,467, which issued to Sweeney on Mar. 22, 1988; U.S. Pat No. 4,453,807, which issued to Faulkner et al. on Jun. 12, 1984; and U.S. Pat. No. 4,820,911, which issued to Arackellian et al. on Apr. 11, 1989.

Examples of filter changers, which may be utilized in accordance with the embodiments of the present invention, may be found in the following U.S. Pat. No. 5,084,761 to Nitta, which issued on Jan. 28, 1992; and U.S. Pat. No. 4,055,846, which issued to to Yamanaka et al. on Oct. 25, 1977.

Examples of photo-optic arrangements and limit switches, which may be utilized in accordance with the embodiments of the present invention, may be found in the following U.S. Pat. No. 5,028,748, which issued to Sakamoto on Jul. 2, 1991; U.S. Pat. No. 5,088,818, which issued to Nicholson on Fe. 18, 1992; U.S. Pat. No. 4,553,842, which issued to Griffin on Nov. 19, 1985; and U.S. Pat. No. 4,139,268, which issued to Litman on Feb. 13, 1979.

Examples of computer arrangements, which may be utilized in accordance with the embodiments of the present invention, may be found in the following U.S. Pat. No. 4,732,467, which issued to Sweeney on Mar. 22, 1988; and U.S. Pat. No. 4,453,807, which issued to Faulkner et al. on Jun. 12, 1984.

In recapitulation, the invention relates to a microscope handling system with a microscope unit, electronic control and evaluation system and an apparatus to load the microscope, including a transport system and a carousel bearing several cassettes containing specimens. The invention can be used in medicine, biology, chemistry, metallurgy and the fabrication of electronic components for the performance of routine inspections. The invention is of particular advantage if a selection of specimens according to defined criteria is required for tedious and time-consuming inspections.

For some time, efforts have been made to automatically load microscopes as efficiently as possible, in particular microscopes intended for the automatic evaluation of specimens. An apparatus to automatically load a microscope is disclosed in U.S. Pat. No. 4,248,498. Here, only one supply cassette is loaded and unloaded, requiring frequent manual intervention in the process to change the supply containers. The microscope unit in the solution disclosed therein is rigidly connected to the transport mechanism and the 3-coordinate table so that a simple adaptation of the handling system to another microscope is essentially not possible. The long specimen advance distances and the relatively long time required to focus the microscope lens tend to result in considerable idle time in the process, during which no image evaluation can take place. In German Patent No. 3,705,166, a process and apparatus for the automatic loading of a microscope is disclosed, in which the use of a rotary table bearing cassettes tends to significantly reduce the frequency of cassette changes. Specimen handling is by means of the vacuum technique often used for the handling of wafers during the manufacture of circuits such as electronic circuits or chips. The complexity of the apparatus is increased by the need for vacuum generation. At the same time, there tends to be a risk of vibration of the specimens and of dust settling on the specimens due to the turbulence of the air.

In the solution just described, the microscope, microscope stage and the transport mechanism also form a solid unit. Thus, sorting of the specimens parallel to image analysis and adaptation of the handling system to another microscope are essentially not possible.

Again, in recapitulation, the invention relates to a microscope handling system with a microscope unit, electronic control and evaluation system and an apparatus to load the microscope, consisting of a transport system and a carousel bearing several cassettes containing specimens. By means of the mechanical separation of the carousel, transport system and microscope unit as taught by the invention, simultaneous, independent movement of the individual components is possible. Thus, tedious routine inspections for which a selection of specimens is necessary can be conducted very quickly and efficiently.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The appended drawings, in their entirety, including all dimensions, proportions and/or shapes in at least one embodiment of the invention, are, if applicable, accurate and to scale and are hereby incorporated by reference into this specification.

The invention as described hereinabove in the context of the preferred embodiments is not to be taken as limited to all of the provided details thereof, since modifications and variations thereof may be made without departing from the spirit and scope of the invention.

What is claimed is:

1. Apparatus for handling biological specimens and for providing the biological specimens to a biological diagnostic device for examination of the biological specimens, which biological specimens are disposed on a plurality of biological receptacle means, said apparatus comprising:

means for storing the biological receptacle means;
 means for, moving the biological receptacle means from said storing means to the biological diagnostic device;
 means for transferring the biological receptacle means from said storing means to said moving means;

means for transferring the biological receptacle means from said moving means to the biological diagnostic device;

said moving means comprising means for rotatably moving the biological receptacle means between said storing means and the biological diagnostic device;

said storing means comprises a plurality of compartments;

each of said plurality of compartments being configured to hold therewithin a plurality of the biological receptacle means; and said moving means comprising:
means for removing a preselected one of the biological receptacle means from one of said plurality of compartments;
means for receiving the preselected one of the biological receptacle means; and
said receiving means for being pivotably mounted between said storing means and the biological diagnostic device.

2. The apparatus according to claim 1, wherein:
said apparatus further comprises means for intermediately positioning the biological receptacle means of one of said compartments in preparation for moving the preselected one of said plurality of biological receptacle means to the biological diagnostic device; and
said receiving means is positionable between a first position, wherein a portion of said receiving means is disposed adjacent said intermediate positioning means and a second position, wherein the same portion of said receiving means is disposed adjacent the biological diagnostic device.

3. Apparatus for handling biological specimens and for providing the biological specimens to a diagnostic device for examination of the biological specimens, which biological specimens are disposed on biological receptacle means, said apparatus comprising:
carousel means;
a plurality of cassettes being disposed on said carousel means, each of said plurality of cassettes being configured to hold a plurality of biological receptacle means;
means for moving the biological receptacle means to the diagnostic device;
said moving means comprising:
means for vertically positioning the biological receptacle means of one of said cassettes in preparation for moving a preselected one of the biological receptacle means to the diagnostic device;
means for removing the preselected one of the biological receptacle means from the same one of said cassettes;
arm means for receiving the preselected one of the biological receptacle means, said arm means for being pivotably mounted between said carousel means and the diagnostic device;
said arm means having a free, pivoting end;
said arm means being configured to pivot between a first position and a second position, wherein, in the first position, said free end is disposed adjacent said vertical positioning means and, in the second position, said free end is disposed adjacent the diagnostic device;

means for transferring the preselected one of the biological receptacle means from said arm means to the diagnostic device;
control means for monitoring the movement of the plurality of biological receptacle means;
said control means comprising:
means for identifying the preselected one of the biological receptacle means during movement of the preselected one of the biological receptacle means between said removing means and the microscope unit; and
feedback means for providing, to said moving means, information regarding the preselected one of the biological receptacle means.

4. The apparatus according to claim 3, wherein:
said carousel means is mounted for rotation;
said apparatus further comprises:
means for driving the rotation of said carousel means; and
means for driving the pivoting of said arm means;
said means for driving the rotation of said carousel means and said means for driving the pivoting of said arm means being configured for providing simultaneous, independent movement of said carousel means and said arm means with respect to one another.

5. The apparatus according to claim 4, wherein:
said cassettes comprise a plurality of holding locations for accommodating the biological receptacle means, each of the biological receptacle means for being disposed in a corresponding one of said holding locations;
said apparatus further comprises means for identifying said holding locations.

6. The apparatus according to claim 5, further comprising:
means for coordinating said means for identifying said holding locations and said means for identifying the preselected one of the biological receptacle means, to determine a one-to-one correspondence between one of said holding locations and the preselected one of the biological receptacle means.

7. The apparatus according to claim 6, wherein the diagnostic device comprises a microscope unit, the biological receptacle means comprise a plurality of slides, said apparatus further comprising:
said means for identifying the preselected one of the biological receptacle means being disposed below a pivoting path of travel of said arm means.

8. The apparatus according to claim 7, wherein:
each of said cassettes comprises an inner portion and a casing portion, said inner portion being slidably disposed within said casing portion and being slidably extractable therefrom, said inner portion being configured to hold the plurality of biological receptacle means corresponding to said cassette;
each of said cassettes comprises means for interlocking said inner portion and said casing portion when said inner portion is fully retracted within said casing portion; and
said means for vertically positioning the biological receptacle means of one of said cassettes comprises means for extracting, in a downward vertical direction, said inner portion of said one of said cassettes from said casing portion of said one of said cassettes.

9. The apparatus according to claim 8, wherein the microscope unit comprises an inverse microscope, said apparatus further comprising:

means for identifying said cassettes during rotation of said carousel;
said means for identifying said cassettes being disposed below a rotational path of travel of said cassettes;
said carousel comprising a plurality of holding areas for holding said cassettes, each of said cassettes for being disposed in a corresponding one of said holding areas;
temporary storage means disposed adjacent the pivoting path of travel of said arm means;
said temporary storage means comprising means for transferring a biological receptacle means between said arm means and said temporary storage means;
said vertical positioning means comprising an arm and motor means for moving said arm in a generally vertical direction;
said vertical positioning means further comprising indexing means for moving said arm to a preselected position corresponding to the preselected one of the biological receptacle means;
each of said inner portions of said cassette means comprising handle means;
said arm of said vertical positioning means having a recessed portion, said recessed portion being configured for slidably accommodating one of said handle means therewithin when the corresponding one of said cassette means is rotated to a position directly above said arm of said vertical positioning means;
said recessed portion of said arm of said vertical positioning means further being configured for confining said one of said handle means in a vertical direction to enable said arm to extract said inner portion of said cassette means from said casing portion of said cassette means;
leaf spring means for restraining the biological receptacle means in said inner portion of one of said cassette means when said inner portion is extracted from said one of said cassette means;
first pusher means for slidably pushing the preselected one of the biological receptacle means from said cassette means onto said arm means;
second pusher means, being mounted on said arm means, for slidably pushing the preselected one of the biological receptacle means from said arm means to the microscope unit;
said second pusher means being configured for slidably pushing a biological receptacle means from said arm means to said temporary storage means;
said temporary storage means comprising third pusher means for slidably pushing a biological receptacle means from said temporary storage means to said arm means;
means for sorting said biological receptacle means, said sorting means comprising means for:
sorting said biological receptacle means within a single one of said cassette means;
sorting said biological receptacle means from one of said cassette means to at least another one of said cassette means; and
said arm means comprising additional leaf spring means for holding a biological receptacle means.

10. Apparatus for handling specimens, and for providing the specimens to an evaluation device for examination of the specimens, said apparatus comprising:
carousel means;
a plurality of cassettes being disposed on said carousel means, each of said plurality of cassettes being configured to hold a plurality of specimens;
means for moving the specimens from said cassettes to the diagnostic device;
said moving means comprising:
means for removing a preselected one of the specimens from one of said cassettes;
arm means for receiving the preselected one of the specimens, said arm means for being pivotably mounted between said carousel means and the evaluation device;
said arm means having a free, pivoting end;
said arm means being configured to pivot between a first position and a second position, wherein, in the first position, said free end is disposed adjacent said vertical positioning means and, in the second position, said free end is disposed adjacent the evaluation device; and
means for transferring the preselected one of the specimens from said arm means to the evaluation device.

11. The apparatus according to claim 10, wherein said removing means comprises means for vertically positioning the specimens of one of said cassettes in preparation for moving the preselected one of the specimens to the evaluation device and means for removing the preselected one of the specimens from the same one of said cassettes.

12. The apparatus according to claim 11, further comprising control means for monitoring the movement of the plurality of specimens.

13. The apparatus according to claim 12, wherein the control means comprises:
means for identifying the preselected one of the specimens during movement of the preselected one of the specimens between said vertical positioning means and the evaluation device; and
feedback means for providing, to said moving means, information regarding the preselected one of the specimens.

14. The apparatus according to claim 13, wherein:
said carousel means is mounted for rotation;
said apparatus further comprises:
means for driving the rotation of said carousel means; and
means for driving the pivoting of said arm means;
said means for driving the rotation of said carousel means and said means for driving the pivoting of said arm means being configured for providing simultaneous, independent movement of said carousel means and said arm means with respect to one another.

15. The apparatus according to claim 14, wherein:
said cassettes comprise a plurality of holding locations for accommodating the specimens, each of the specimens for being disposed in a corresponding one of said holding locations;
said apparatus further comprises means for identifying said holding locations.

16. The apparatus according to claim 15, further comprising:
means for coordinating said means for identifying said holding locations and said means for identifying the preselected one of the specimens, to determine a one-to-one correspondence between one of said holding locations and the preselected one of the specimens.

17. The apparatus according to claim 16, wherein the evaluation device is a diagnostic device, the diagnostic device comprises a microscope unit, the specimens are disposed on biological receptacle means, the biological receptacle means comprise a plurality of slides, said apparatus further comprising:
said means for identifying the preselected one of the biological receptacle means being disposed below a pivoting path of travel of said arm means.

18. The apparatus according to claim 17, wherein:
each of said cassettes comprises an inner portion and a casing portion, said inner portion being slidably disposed within said casing portion and being slidably extractable therefrom said inner portion being configured to hold the plurality of biological receptacle means corresponding to said cassette;
each of said cassettes comprises means for interlocking said inner portion and said casing portion when said inner portion is fully retracted within said casing portion; and
said means for vertically positioning the biological receptacle means of one of said cassettes comprises means for extracting, in a downward vertical direction, said inner portion of said one of said cassettes from said casing portion of said one of said cassettes.

19. The apparatus according to claim 18, wherein the microscope unit comprises an inverse microscope, said apparatus further comprising:
means for identifying said cassettes during rotation of said carousel;
said means for identifying said cassettes being disposed below a rotational path of travel of said cassettes;
said carousel comprising a plurality of holding areas for holding said cassettes, each of said cassettes for being disposed in a corresponding one of said holding areas;
temporary storage means disposed adjacent the pivoting path of travel of said arm means;
said temporary storage means comprising means for transferring a biological receptacle means between said arm means and said temporary storage means;
said vertical positioning means comprising an arm and motor means for moving said arm in a generally vertical direction;
said vertical positioning means further comprising indexing means for moving said arm to a preselected position corresponding to the preselected one of the biological receptacle means;
each of said inner portions of said cassette means comprising handle means;
said arm of said vertical positioning means having a recessed portion, said recessed portion being configured for slidably accommodating one of said handle means therewithin when the corresponding one of said cassette means is rotated to a position directly above said arm of said vertical positioning means;
said recessed portion of said arm of said vertical positioning means further being configured for confining said one of said handle means in a vertical direction to enable said arm to extract said inner portion of said cassette means from said casing portion of said cassette means;
leaf spring means for restraining the biological receptacle means in said inner portion of one of said cassette means when said inner portion is extracted from said one of said cassette means;
first pusher means for slidably pushing the preselected one of the biological receptacle means from said cassette means onto said arm means;
second pusher means, being mounted on said arm means, for slidably pushing the preselected one of the biological receptacle means from said arm means to the microscope unit;
said second pusher means being configured for slidably pushing a biological receptacle means from said arm means to said temporary storage means;
said temporary storage means comprising third pusher means for slidably pushing a biological receptacle means from said temporary storage means to said arm means;
means for sorting said biological receptacle means, said sorting means comprising means for:
sorting said biological receptacle means within a single one of said cassette means;
sorting said biological receptacle means from one of said cassette means to at least another one of said cassette means; and
said arm means comprising additional leaf spring means for holding a biological receptacle means.

* * * * *